United States Patent [19]
Frigola-Constansa et al.

[11] Patent Number: 5,849,931
[45] Date of Patent: Dec. 15, 1998

[54] PROCESS FOR SEPARATING CARBINOLS

[75] Inventors: Jordi Frigola-Constansa, Barcelona; Juana Maria Berrocal Romero, Cornella De Llobregat; Maria Rosa Cuberes Altisent, Saint Cugat del Valles; Vicente Gotor Santamaria, Oviedo, all of Spain

[73] Assignee: Laboratorios Del Dr. Esteve S.A., Barcelona, Spain

[21] Appl. No.: 875,806

[22] PCT Filed: Dec. 4, 1997

[86] PCT No.: PCT/EP96/05596

§ 371 Date: Aug. 5, 1997

§ 102(e) Date: Aug. 5, 1997

[87] PCT Pub. No.: WO97/20817

PCT Pub. Date: Jun. 12, 1997

[30]     Foreign Application Priority Data

Dec. 6, 1995  [FR]   France .................................. 95 14414

[51] Int. Cl.$^6$ .................................................. C07D 231/12
[52] U.S. Cl. ............................................. 548/376.1
[58] Field of Search ............................................ 548/376.1

[56]         References Cited

U.S. PATENT DOCUMENTS 4,963,492   10/1990   Keller et al. .

OTHER PUBLICATIONS

Chemical Abstracts, vol. 119, No. 7, Aug. 16, 1993, Abstract No. 72535b, Hueso–Rodriguez, J.A., et al., "Preparation of the enantiomers of the analgesic E–3710", 2 pages.

*Primary Examiner*—Robert W. Ramsuer
*Attorney, Agent, or Firm*—Rockey, Milnamow & Katz, Ltd.

[57]         ABSTRACT

A method for predominantly preparing the enantiomer (R)-(+)-5-(phenyl)hydroxymethyl-1-methyl-1H-pyrazole, (R)-(+)-1, by separating the racemate (+)-5-(phenyl)hydroxymethyl-1-methyl-1H-pyrazole of formula (1), comprising the series of steps of using a lipase or material derived therefrom having enzymatic activity in a transesterification reaction, as well as hydrolysing the resulting ester, (S)-(-)-5-(phenyl)alkylcarbonyloxymethyl-1-methyl-1H-pyrazole, of formula (S)-(-)-4, wherein $R_1$ is a methyl or ethyl radical.

8 Claims, No Drawings

PROCESS FOR SEPARATING CARBINOLS

This application is a 371 of PCT/EP96/05596 filed Dec. 4, 1996.

The present invention relates to a new process for separating a carbinol of formula 1 into its enantiomers, as well as the racemization of one of the latter, by performing a sequential process with the object of obtaining the desired enantiomer in high yield. The stereoisomers of 1 are the key compounds for the synthesis of the enantiomers of the compound of formula 2

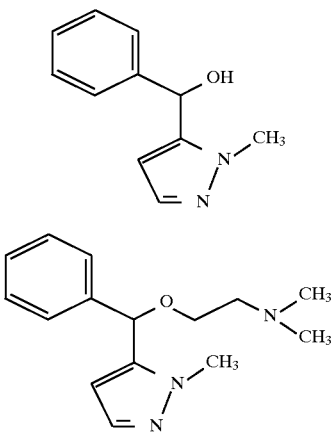

(±)-5-{[(N,N-Dimethylaminoethoxy)phenyl]methyl}-1-methyl-1H-pyrazole, of formula 2, is a compound with analgesic properties, currently in the clinical study phase, described in European Patent EP 289 380. Both enantiomers of 2 have been synthesized and evaluated as analgesics [J. A. Hueso, J. Berrocal, B. Gutiérrez, A. J. Farré and J. Frigola, Bioorganic & Medicinal Chemistry Letters, 1993, 3, 269–272], and the outcome of this has been that the dextrorotatory enantiomer is the more active.

The enantiomers (+)-2 and (−)-2 are obtained, respectively, by alkylation of (+)-1 and (−)-1. The stereoisomer (+)-1 has been obtained in a very low yield from ethyl (R)-mandelate, which has determined in this way the absolute configuration (R)-(+)-1. The enantiomers of 1 have also been obtained by complex processes of separation by column chromatography or of fractional crystallizations of the diastereoisomeric esters formed by reacting 1 with (+)-O-acetylmandelic acid. The yields were 22% for the enantiomer (−)-1 and 25% for the enantiomer (+)-1.

In addition, the use of biocatalysts applied to the separation of racemic mixtures has been amply described [a) "Microbial reagents in organic synthesis", edited by Stefano Servi, Kluwer Academic Publishers, London, 1992. b) "Enzymes in synthetic organic chemistry" edited by C. H. Wong and G. M. Whitesides, Elsevier Science, Oxford 1994. c) "Biotransformations in Organic Chemistry", edited by K. Faber, Lange and Springer, 1995].

There are many different classes of enzymes used for the separation of stereoisomers, including hydrolases (especially lipases, proteases and esterases), liases and oxidoreductases. Hydrolases are among the most attractive enzymes to be used in the separations, since they are commercially available at low cost and some of them show a reasonable tolerance to organic solvents.

The use of organic solvents in enzyme-catalyzed reactions has various advantages: a) most organic substrates are more soluble in organic solvents than in water; b) recovery of the reaction products is facilitated to an exceptional extent; c) the enzymes are readily collected to be reused; d) in some cases, the enantioselectivity is high. In spite of the advantages of using enzymes in organic solvents, there are also, however, some disadvantages; a) the search for a suitable solvent; b) the low speed of reaction; c) the decrease in the optical purity of the desired product in these reactions of a reversible nature [for a review see: a) A. M. Klibanov, Trends Biochem. Sci., 1989, 14, 141. b) C. S. Chen, C. J. Sih, Angew. Chem. Int. Ed. Engl., 1989, 28, 695]. The conclusive finding that some enzymes can act in organic solvents has been one of the main causes of the spectacular increase, during the last decade, in the use of biotransformations for the preparation of products of therapeutic and industrial interest [for a review see: a) A. N. Collins, G. N. Sheldrake, S. Crosby, "Chirality in Industry", Wiley, London, 1992. b) S. C. Stinson, Chem. & Eng. News, 1994, 38. c) A. L. Margolin, Enzyme Microb. Technol. 1993, 15, 266].

The subject of the present invention consists in providing a commercially usable process for obtaining the dextrorotatory stereoisomer (R)-(+)-1, which process could also be usable for obtaining the levorotatory stereoisomer (S)-(−)-1.

The process to which the present invention relates is based on biocatalysis, using a biocatalyst to perform selectively a transesterification between the racemic alcohol 1 and an ester of formula 3, in which $R_1$ represents a methyl or ethyl radical and $R_2$ represents a vinyl or isopropenyl radical. By means of an enzyme which permits the appropriate stereo-selectivity, it is possible to obtain a reaction mixture which contains the unreacted enantiomer of 1 at the same time as the ester of formula 4, in which $R_1$ represents a methyl or ethyl radical, formed from the other enantiomer of 1.

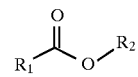

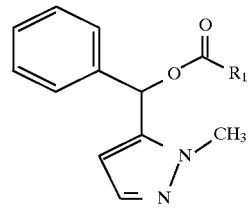

The separation and recovery of the unreacted alcohol and of the ester formed hence enables conventional chemical methods such as chromatography or crystallization to be used relatively easily. Another aspect of the invention consists in performing the hydrolysis of the ester obtained using an acidic or basic catalyst, so as to bring about a racemization, thereby recovering the compound 1, or the retention of the configuration. In the case where the racemic mixture 1 is obtained, the latter can then be treated with the abovementioned biocatalyst to give rise to a transesterification process as described above, and so on. In this way, an almost complete conversion of the racemic substrate 1 is obtained, giving the desired enantiomer.

The strategy used in the present invention consists of the sequential combination of an enzymatic transesterification of the carbinol 1 and a chemical conversion with racemization. The most suitable enzymes for performing the transesterification are hydrolases, chiefly the lipases produced by microorganisms, the enzymes being either free or immobilized. The esters used as acylating agents are the enol esters of formula 3 in which $R_1$ represents a methyl or ethyl radical and $R_2$ represents a vinyl or isopropenyl radical. The transesterification reaction is performed in the absence of a solvent or in a suitable solvent such as hexane, cyclohexane, toluene, acetone, dioxane, tetrahydrofuran, ethanol, and the like, at a temperature between 20° C. and the refluxing temperature, for the time needed to bring about the conversion, it being possible for this time to fluctuate between 6 hours and 48 hours. The addition of molecular sieves to the reaction medium can increase the activity and decrease the water content. The progression of the acylation reaction is readily monitored by proton nuclear magnetic resonance. The unreacted enantiomer of 1 is separated from the other, esterified enantiomer 4 by column chromatography on silica gel or by crystallization in a suitable solvent. The optical purity is analyzed by chiral HPLC (high performance liquid chromatography).

The esterified enantiomer 4 is hydrolyzed to give rise thereafter to the formation of the racemic carbinol 1 or of the corresponding homochiral carbinol. The hydrolysis is performed, respectively, in an acid medium or in a basic medium, at a temperature between 60° C. and the refluxing temperature, for a time between 2 and 24 hours.

By alkylation of the stereoisomers (+)-1 and (−)-1 with dimethylaminochloroethane under phase transfer conditions, and by subsequent treatment with citric acid, the stereoisomers (+)-2.citrate and (−)-2.citrate, respectively, are obtained.

The description which precedes the process of transesterification of the racemic carbinol 1 to obtain a homochiral carbinol and of the hydrolysis of the homochiral ester formed to obtain the corresponding homochiral alcohol or alternatively the racemic alcohol, as well as the detailed description of the examples which appear below, given only by way of illustration, can in no way limit the scope of the present invention.

EXAMPLE 1

Separation of (±)-5-(phenyl)hydroxymethyl-1-methyl-1H-pyrazole, (±)-1, with lypase PS:

A mixture of 100 g of carbinol ( )-1, 50 g of activated lypase PS, marketed by AMANO PHARMACEUTICAL COMPANY Ltd. (NAGOYA-JP), 50 g of activated 3 Å molecular sieves and 1000 ml of vinyl acetate is stirred at 60° C. for 24 hours. After verification by 1H NMR that the substrate has been acetylated to the extent of 55%, the mixture is filtered to collect the lipase and the molecular sieves and the vinyl acetate is evaporated off under reduced pressure. The residue is dissolved in cyclohexane, from which 36 g (72%) of (+)-5-(phenyl) hydroxymethyl-1-methyl-1H-pyrazole, (+)-1, with an optical purity of greater than 96% (enantiomeric excess determined by HPLC=92%) are obtained by crystallization; melting point: 80°–83° C.; IR (KBr) 3237, 1456, 1394, 1294, 1193, 1058, 1006, 785, 765, 708, 701 cm$^{-1}$; $[\alpha]_D$+16.2 (c=1, CHCl$_3$). Evaporation of the solvent gives 76.5 g of, preponderantly, (−)-5-(phenyl)methylcarbonyloxymethyl-1-methyl-1H-pyrazole, (−)-4, where R$_1$ represents a methyl radical.

EXAMPLE 2

Hydrolysis and racemization of (−)-5-(phenyl)methylcarbonyloxymethyl-1-methyl-1H-pyrazole, (−)-4:

76.5 g of (−)-5-(phenyl)methylcarbonyloxymethyl-1-methyl-1H-pyrazole, (−)-4, are refluxed in 300 ml of 6N hydrochloric acid for 12 hours, the mixture is filtered while heating and the solution is alkalinized with ammonium hydroxide to obtain 61.4 g of racemic carbinol (±)-5-(phenyl)hydroxymethyl-1-methyl-1H-pyrazole, (±)-1, melting point 105°–106° C.; IR (KBr) 3225, 1457, 1398, 1208, 1200, 1018, 1009, 794, 751, 702 cm$^{-1}$; enantiomeric excess determined by HPLC=0.

EXAMPLE 3

Separation of (±)-5-(phenyl)hydroxymethyl-1-methyl-1H-pyrazole, (±)-1, with lipase PS:

A mixture of 61.4 g of carbinol (+)-1 obtained in Example 2, 30.7 g of activated lipase PS, marketed by AMANO PHARMACEUTICAL COMPANY Ltd. (NAGOYA-JP), 30.7 g of activated 3 Å molecular sieves and 600 ml of vinyl acetate are stirred at 56° C. for 36 hours. After verification with H NMR that the substrate has been acetylated to the extent of 53%, the mixture is filtered to collect the lipase and the molecular sieves and the vinyl acetate is evaporated off under reduced pressure. The residue is dissolved in cyclohexane, from which 21.7 g (71%) of (+)-5-(phenyl)hydroxymethyl-1-methyl-1H-pyrazole, (+)-1, with an optical purity of greater than 95%, is obtained by crystallization, melting point: 79°–85° C. $[\alpha]_D$+16.0 (c=1, CHCl$_3$). Evaporation of the solvent gives 45.8 g of, preponderantly, (−)-5-(phenyl)methylcarbonyloxymethyl-1-methyl-1H-pyrazole, (−)-4, where R$_1$ represents a methyl radical.

EXAMPLE 4

Separation of (+)-5-(phenyl)hydroxymethyl-1-methyl-1H-pyrazole, (±)-1, with lipase PS:

A mixture of 3.5 g of carbinol (+)-1, 7.4 g of activated lipase PS, marketed by AMANO PHARMACEUTICAL COMPANY Ltd. (NAGOYA-JP) and 100 ml of vinyl acetate is stirred at 62° C. for 13 hours. After verification by 1H NMR that the substrate has been acetylated to the extent of 50%, the mixture is filtered to collect the lipase and the molecular sieves and the vinyl acetate is evaporated off under reduced pressure. The residue is chromatographed on a column with silica gel, eluting with diethyl ether/hexane (2:1) to obtain 2.1 g (98%) of (−)-5-(phenyl)methylcarbonyloxymethyl-1-methyl-1H-pyrazole, (−)-4, where R$_1$ represents a methyl radical. By then eluting with diethyl ether, 1.7 g (98%) of (+)-5-(phenyl)hydroxymethyl-1-methyl-1H-pyrazole, (+)-1, is obtained, with an enantiomeric excess determined by HPLC=94%.

EXAMPLE 5

Hydrolysis with retention of configuration of (−)-5-(phenyl)methylcarbonyloxymethyl-1-methyl-1H-pyrazole, (−)-4:

2.3 g of (−)-5-(phenyl)methylcarbonyloxymethyl-1-methyl-1H-pyrazole, (−)-4, are refluxed in 4 ml of 20% sodium hydroxide and 10 ml of ethanol for 2 hours, the ethanol is evaporated off, 10 ml of water are added, the mixture is extracted with diethyl ether, the organic phase is dried with magnesium sulfate and filtered and, from the solution, 1.8 g (95%) g of (−)-5-(phenyl)hydroxymethyl-1-methyl-1H-pyrazole, (−)-1, is obtained with an optical purity of greater than 94%, $[\alpha]_D$−16.1 (c=1, CHCl$_3$).

EXAMPLE 6

Production of (+)-5-{[(N,N-dimetylaminoethoxy)phenyl]methyl}-1-methyl-1H-pyrazole citrate, (+)-2.citrate.

A mixture of 12.7 g of (+)-5-(phenyl)hydroxymethyl-1-methyl-1H-pyrazole, (+)-1, in 250 ml of toluene, 125 ml of 50% sodium hydroxide, 3 g of trietylbutylamonium and 14.6 g of dimethylaminochloroethane hydrochloride is refluxed for 7 hours. From the cold mixture, 16.2 g (92.6%) of (+)-5-{[(N,N-dimethylaminoethoxy)phenyl]methyl}-1-methyl-1H-pyrazole, (+)-2, are extracted with toluene.

A mixture of 15 g of (+)-5-{[(N,N-dimethylaminoethoxy)-phenyl]methyl}-1-methyl-1H-pyrazole, (+)-2, and 13.5 g of citric acid monohydrate in ethanol is stirred at 40° C. until dissolution is complete. From this solution, 24.7 g (94.5%) of (+)-5-{[(N,N-dimethylaminoethoxy)-phenyl]methyl}-1-methyl-1H-pyrazole citrate, (+)-2.citrate, are recovered by crystallization, melting point 129°–131° C., $[\alpha]_D$+8.3 (c=1, H$_2$O).

EXAMPLE 7

Production of (−)-5-{[(N,N-dimethylaminoethoxy)phenyl]-methyl}-1-methyl-1H-pyrazole citrate, (−)-2.citrate.

By a procedure similar to that of example 6, and using the enantiomer (−)-5-(phenyl)hydroxymethyl-1-methyl-1H-pyrazole, (−)-1, as separation product, (−)-5-{[(N,N-dimethylaminoethoxy)phenyl]methyl}-1-methyl-1H-pyrazole, (−)-2.citrate, is obtained, melting point 128°–130° C. $[\alpha]_D$ −8.2 (c=1, $H_2O$).

We claim:

1. Process for preparing preponderantly the enantiomer (R)-(+)-5-(phenyl)hydroxymethyl-1H-pyrazole, (R)-(+)-1, by separation of the racemic mixture (±)-5-(phenyl)hydroxymethyl-1-methyl-1H-pyrazole, of formula 1, which comprises reacting a lipase in a transesterification reaction, followed by the hydrolysis of the ester formed, (S)-(−)-5-(phenyl)alkylcarbonyloxymethyl-1 methyl-1H-pyrazole, of formula (S)-(−)-4 in which $R_1$ represents a methyl or ethyl radical

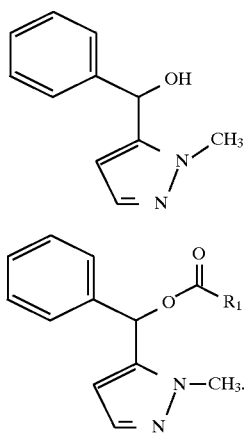

2. Process according to claim 1, wherein a lipase acts as a catalyst in a transesterification reaction between an ester of formula 3, in which $R_1$ represents a methyl or ethyl radical and $R_2$ represents a vinyl or isopropenyl radical, and the enantiomer (S)-(−)-5-(phenyl)hydroxymethyl-1-methyl-1H-pyrazole, (S)-(−)-1, which gives rise to the formation of (S)-(−)-5-(phenyl)alkylcarbonyloxymethyl-1-methyl-1H-pyrazole, of formula (S)-(−)-4 in which $R_1$ represents a methyl or ethyl radical, and recovering the unreacted enantiomer (R)-(+)-5-(phenyl)hydroxymethyl-1-methyl-1H-pyrazole,(R)-(+)-1,

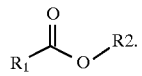

3. Process according to claim 2 wherein vinyl acetate of formula 3, in which $R_1$ represents a methyl radical and $R_2$ represents a vinyl radical, as reactant and as solvent in the transesterification reaction.

4. Process according to claim 1 wherein a solvent of low polarity is used to crystallize the enantiomer (R)-(+)-5-(phenyl)hydroxymethyl-1-methyl-1H-pyrazole, (R)-(+)-1, from the solution which contains, in addition, the ester (S)-(−)-5-(phenyl)methylcarbonyloxymethyl-1-methyl-1H-pyrazole, of formula (S)-(−)-4 in which $R_1$ represents a methyl radical.

5. Process according to claim 1 wherein column chromatography on silica gel is performed to separate the carbinol (R)-(+)-5-(phenyl)hydroxymethyl-1-methyl-1H-pyrazole, (R)-(+)-1, from the ester (S)-(−)-5-(phenyl)methylcarbonyloxymethyl-1-methyl-1H-pyrazole, of formula (S)-(−)-4 in which $R_1$ represents a methyl radical.

6. Process according to claim 1 wherein the hydrolysis of the ester (S)-(−)-5-(phenyl)alkylcarbonyloxymethyl-1-methyl-1H-pyrazole, of formula (S)-(−)-4 in which $R_1$ represents a methyl or ethyl radical, is performed in an acid medium, to obtain the racemic mixture (±)-5-(phenyl) hydroxymethyl-1-methyl-1H-pyrazole, of formula 1, which, is optionally repeatedly subjected to a process of separation which may be repeated.

7. Process according to claim 1 wherein the hydrolysis of the ester (S)-(−)-5-(phenyl)alkylcarbonyloxymethyl-1-methyl-1H-pyrazole, of formula (S)-(−)-4, in which $R_1$ represents a methyl or ethyl radical, is performed with retention of the configuration in a basic medium, to obtain (S)-(−)-5-(phenyl)hydroxymethyl-1-methyl-1H-pyrazole, of formula (S)-1.

8. Process according to claim 4 wherein the solvent is cyclohexane.

* * * * *

UNITED STATES PATENT AND TRADEMARK OFFICE
CERTIFICATE OF CORRECTION

PATENT NO. : 5,849,931
DATED       : December 15, 1998
INVENTOR(S) : Jordi Frigola-Constansa, et al.

It is certified that error appears in the above-identified patent and that said Letters Patent is hereby corrected as shown below:

Claim 3, lines 1 and 2, "vinyl acetate of formula 3, in which" should be deleted.

Signed and Sealed this

Thirtieth Day of March, 1999

Attest:

Q. TODD DICKINSON

*Attesting Officer*    *Acting Commissioner of Patents and Trademarks*